US009974370B2

United States Patent
Winterton et al.

(10) Patent No.: US 9,974,370 B2
(45) Date of Patent: *May 22, 2018

(54) PRESSURE-VENTING CONTAINER

(71) Applicant: Better Vision Solutions LLC, Keller, TX (US)

(72) Inventors: Lynn Winterton, Keller, TX (US); Jack White, Alpharetta, GA (US)

(73) Assignee: Better Vision Solutions LLC, Keller, TX (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/355,479

(22) Filed: Nov. 18, 2016

(65) Prior Publication Data

US 2017/0065046 A1    Mar. 9, 2017

Related U.S. Application Data

(63) Continuation of application No. 14/707,097, filed on May 8, 2015, now Pat. No. 9,532,632.

(51) Int. Cl.
*A45C 11/00* (2006.01)
*B65D 25/38* (2006.01)
*B65D 81/22* (2006.01)
*A61L 12/08* (2006.01)
*A45C 13/02* (2006.01)
*B65D 47/32* (2006.01)
*B65D 51/26* (2006.01)

(52) U.S. Cl.
CPC ............ *A45C 11/005* (2013.01); *A45C 13/02* (2013.01); *A61L 12/086* (2013.01); *B65D 25/38* (2013.01); *B65D 47/32* (2013.01); *B65D 51/26* (2013.01); *B65D 81/22* (2013.01)

(58) Field of Classification Search
CPC ....... A45C 11/00; A45C 11/005; A45C 11/04; A45C 13/02; B65D 25/38; B65D 81/22
USPC ..... 206/5.1; 134/18, 901; 422/113, 300, 301
See application file for complete search history.

(56) References Cited

U.S. PATENT DOCUMENTS

| 4,750,610 A | * | 6/1988 | Ryder | A45C 11/005 134/901 |
| 4,956,156 A | * | 9/1990 | Kanner | A45C 11/005 206/438 |
| 5,250,266 A | * | 10/1993 | Kanner | A45C 11/005 134/901 |
| 5,283,053 A | * | 2/1994 | Kamiya | A61L 12/02 134/105 |
| 5,366,078 A | | 11/1994 | Braun | |
| 5,558,846 A | * | 9/1996 | Alvord | A45C 11/005 134/901 |

(Continued)

OTHER PUBLICATIONS

International Search Report & Written Opinion, dated Jun. 28, 2016 cited in PCT/US2016/031026, 11 pages.

*Primary Examiner* — Bryon Gehman
(74) *Attorney, Agent, or Firm* — Merchant & Gould P.C.

(57) ABSTRACT

A system for releasing a contained volume of gas. The system has a base with a pressure-release vent positioned within a flex region and a seal to disengagably seal the pressure-release vent. The seal has a gas vent path that extends from the pressure-release vent. The contained volume of gas passes through the gas vent path to apply force against the flex region and disengage the seal from the pressure-release vent, allowing the gas to exit through the pressure-release vent.

6 Claims, 13 Drawing Sheets

(56) References Cited

U.S. PATENT DOCUMENTS

| | | | |
|---|---|---|---|
| 6,000,534 | A | 12/1999 | Koomruian |
| 6,945,389 | B2 | 9/2005 | Scherer et al. |
| 8,113,341 | B2 * | 2/2012 | Kanner ................ A45C 11/005 134/901 |
| 8,141,699 | B2 | 3/2012 | Kanner et al. |
| 8,329,113 | B2 * | 12/2012 | Kanner ................ A45C 11/005 422/292 |
| 8,410,011 | B2 | 4/2013 | Huddersman et al. |
| 8,513,303 | B2 | 8/2013 | Huddersman et al. |
| 8,757,367 | B2 | 6/2014 | Winterton et al. |
| 8,767,367 | B2 | 7/2014 | Higuchi et al. |
| 9,174,208 | B2 | 11/2015 | Huddersman |
| 2010/0233023 | A1 | 9/2010 | Kanner |
| 2016/0324287 | A1 | 11/2016 | Winterton |

* cited by examiner

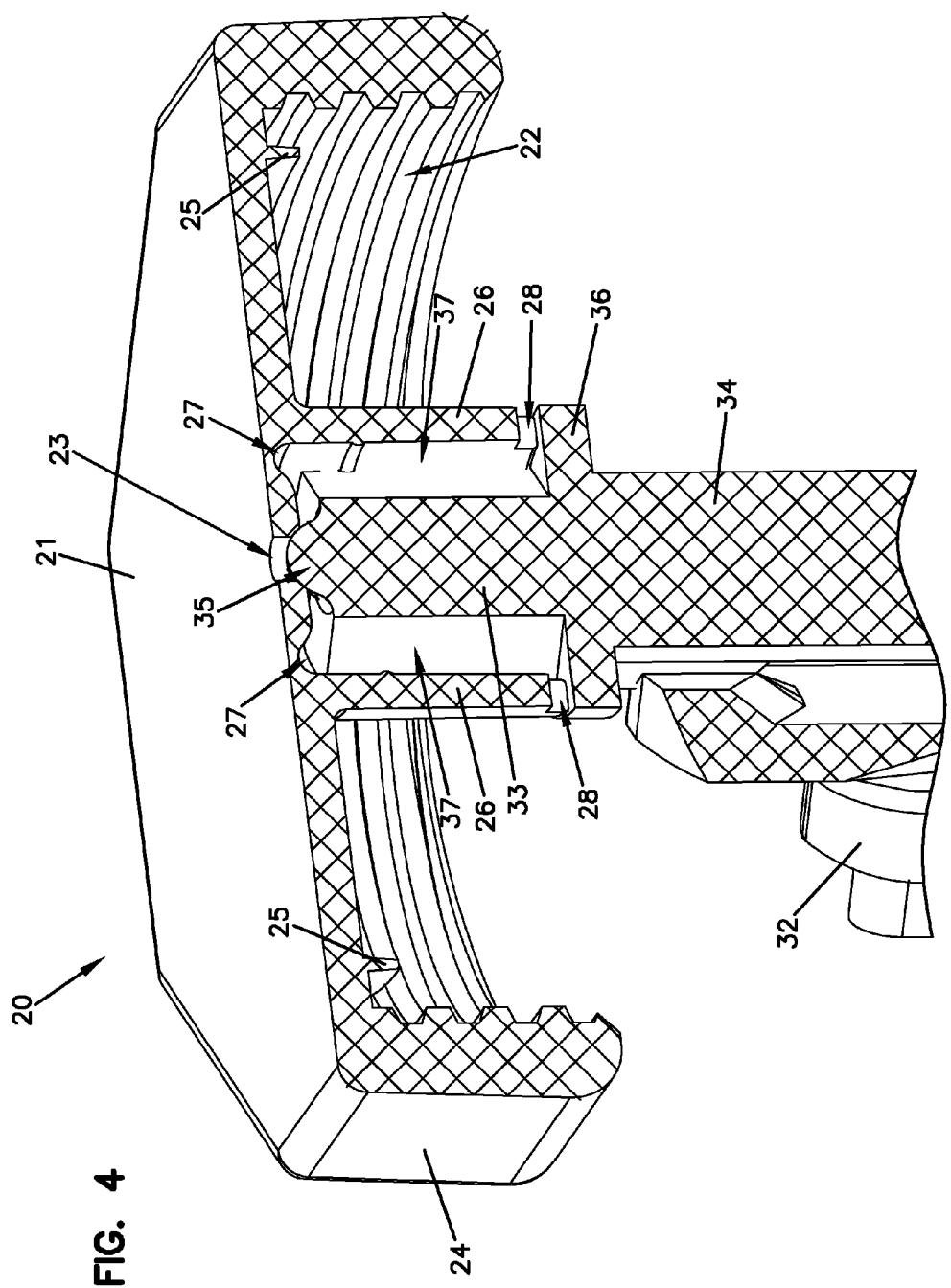

PRESSURE-VENTING CONTAINER

CROSS-REFERENCE TO RELATED APPLICATION

This application is a continuation of U.S. patent application Ser. No. 14/707,097, filed May 8, 2015, which is entirely incorporated herein by reference.

TECHNICAL FIELD

The present disclosure relates generally to the field of lens care, and more particularly to a container for disinfection and storage of contact lenses.

BACKGROUND

Contact lens containers of various styles and functionality are utilized for storing, cleaning and/or disinfecting contact lenses. In some lens containment and care systems a hydrogen peroxide based lens care solution is used, wherein the contact lenses to be cleaned and/or disinfected are deposited in contact with the hydrogen peroxide solution for a certain period of time, in order that cleaning and/or disinfecting of the contact lenses can take place to a satisfactory extent. The contact lens containers utilized in such lens care systems typically comprise closable baskets, which open to receive the contact lenses to be cleaned and close to retain the lenses during treatment. The baskets are typically part of a contact lens holder component, which in turn can be connected to the cap of a contact lens container, for example via a stern or rib. Before the cap is placed onto the container cup, the container cup is dosed to a prescribed fill level with a hydrogen peroxide lens care solution. A catalyst tablet, for example catalase which gives delayed release of catalase, can be added to the container cup before or after adding the hydrogen peroxide solution. Finally, the contact lens holder containing the lenses to be treated is immersed into the hydrogen peroxide solution in the container cup, and the container is closed by screwing the cap onto the container cup.

The closure of the cap on the container cup may form a water-tight seal, to prevent leakage of the cleaning solution. The contact lenses are allowed to remain immersed in the solution for a period of time sufficient to complete the specified cleaning and/or disinfecting process. The oxygen produced from decomposition of hydrogen peroxide in the cleaning solution typically must be allowed to discharge from the container in some manner. Attempts to provide oxygen discharge exist, for example U.S. Pat. No. 6,945,389 and U.S. Pat. No. 8,757,367.

Continued improvements to lens care systems for cleaning, disinfecting and storing contact lenses are desired. It is to the provision of improved lens care systems that the present invention is primarily directed.

SUMMARY

Aspects of the present disclosure relate to a lens care container for cleaning with cleaning solution. The lens care container includes a container cup defining an interior chamber accessible through an opening bounded by a rim having an outer diameter. The container cup is configured to hold the lens cleaning solution. The cap can be removably attachable to the container cup to cover the opening. The cap can further include a top panel, a coupling hub, and a collar having an inner diameter extending transversely from the top panel. The inner diameter can be configured to receive the container cup outer diameter. The top panel can include a pressure-release vent positioned within a deflection region. The coupling hub can define an interior gas vent path that extends from the top panel and bounded by an anti-rotation mechanism and at least one channel. The lens holder can include a stem having an anti-rotation mechanism that cooperates with the cap anti-rotation mechanism. The interaction between the stem anti-rotation mechanism and the cap anti-rotation mechanism can prevent rotation of the cap with respect to the lens holder. The lens holder can also include a seal which can sealably engage the cap pressure-release vent when the cap and lens holder are received within the container cup. During a disinfection process, a volume of gas generated from the cleaning solution passes through the at least one channel vent into the interior gas vent path to apply force against the deflection region and disengage the lens holder seal from the cap pressure-release vent to allow the gas to exit through the cap pressure-release vent.

Another aspect of the present disclosure relates to a system for releasing a volume of gas from a container that has a contained volume and a connector. The system includes a base that is removably connected to the container connector. The base includes a pressure-release vent that is positioned within a flex region. The system also includes a seal to disengagably seal the pressure-release vent. The seal includes a gas vent path that extends from the pressure-release vent into the container contained volume. The volume of gas passes through the gas vent path to apply force against the flex region and disengage the lens holder seal from the cap pressure-release vent, allowing the gas to exit through the cap pressure-release vent.

A still further aspect of the present disclosure relates to a system for releasing a volume of gas from a container that includes a contained volume and a connector. The system includes a cap that is removably attachable to the container cup connector to enclose the volume of gas. The cap includes a top panel that includes a pressure-release vent positioned within a deflection region. The system also includes a coupling hub that includes a seal to removably seal the pressure-release vent, and an interior gas vent path extending from the top panel and bounded by at least one channel vent. The volume of gas passes through the at least one channel vent into the interior gas vent path to apply force against the deflection region and unseal the lens holder seal from the cap pressure-release vent, allowing the gas to exit through the cap pressure-release vent.

A still further aspect of the present disclosure relates to a system for releasing a contained volume of gas. The system has a base with a pressure-release vent positioned within a flex region and a seal to disengagably seal the pressure-release vent. The seal has a gas vent path that extends from the pressure-release vent. The contained volume of gas passes through the gas vent path to apply force against the flex region and disengage the seal from the pressure-release vent, allowing the gas to exit through the pressure-release vent.

A still further aspect of the present disclosure relates to a lens care container with a container defining an interior chamber and a cap which is removably attachable to the container. The cap has a pressure-release vent positioned within a deflection region. The lens care container also has and a lens holder with a seal to sealably engage the cap pressure-release vent.

BRIEF DESCRIPTION OF THE DRAWINGS

FIG. 4 is a perspective cross sectional view of the cap component of the lens care system of FIG. 1.

DESCRIPTION

Figure 1:
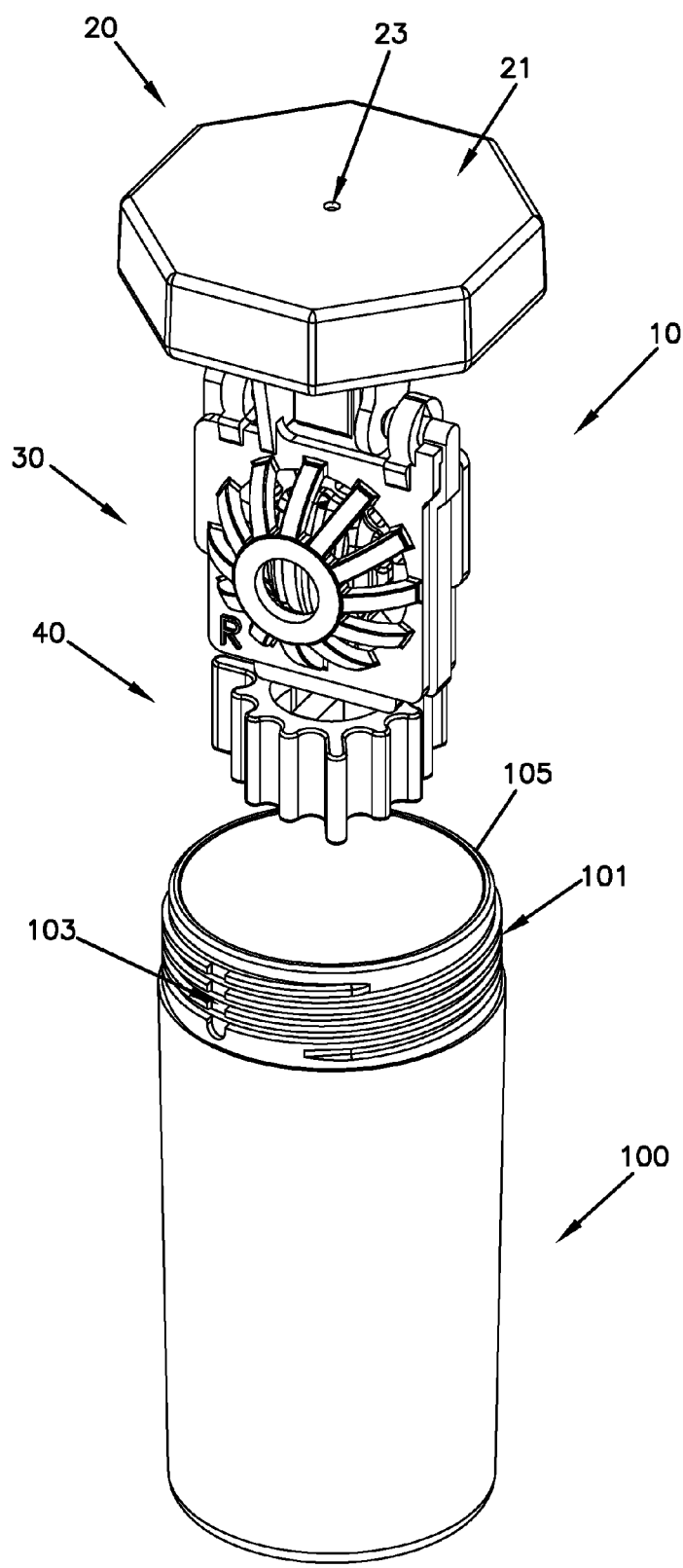
FIG. 1 is a perspective assembly view of a lens care system according to an example embodiment of the present disclosure.
Figure 2:
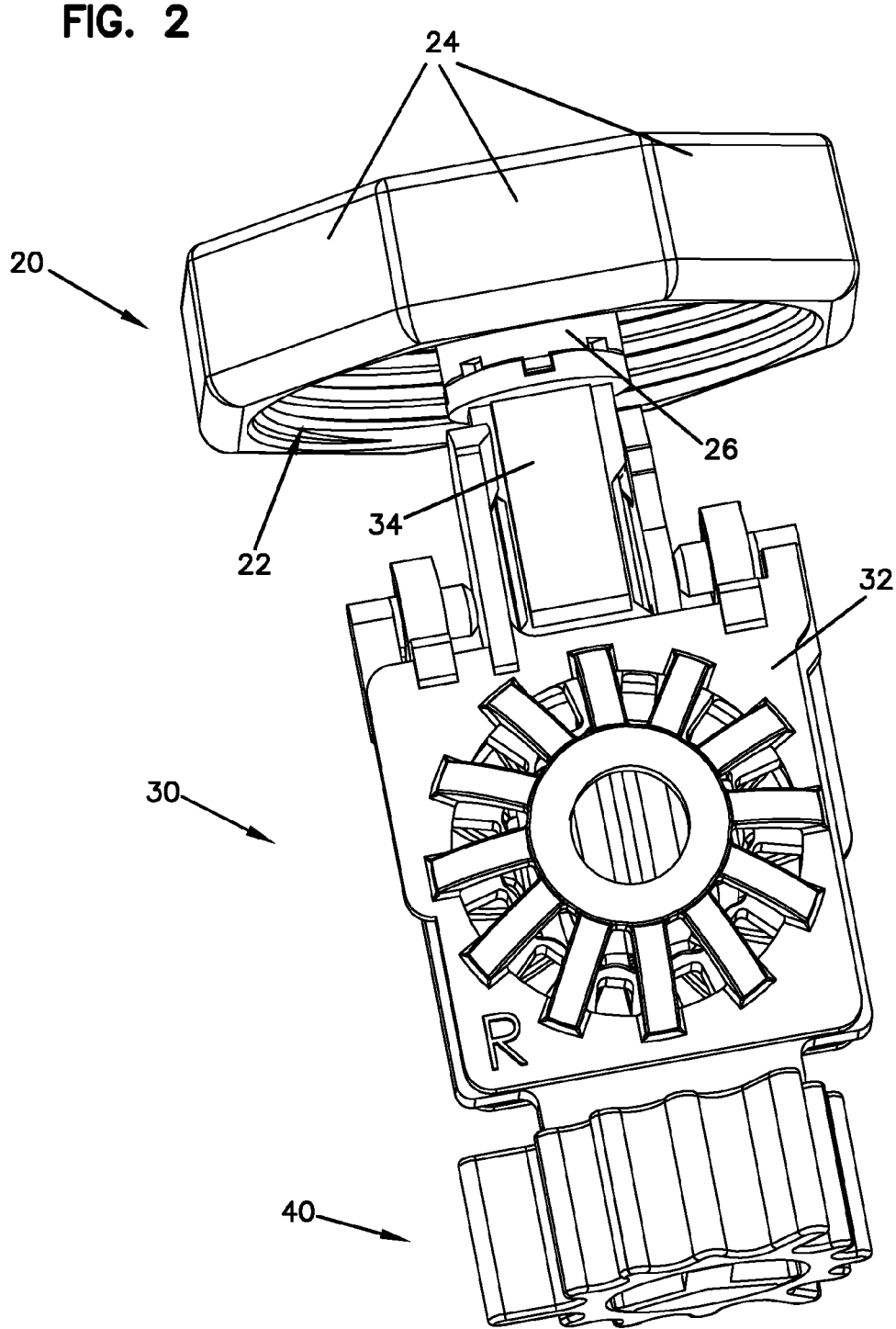
FIG. 2 is a perspective view of the contact lens holder component of the lens care system shown in FIG. 1.
Figure 3:
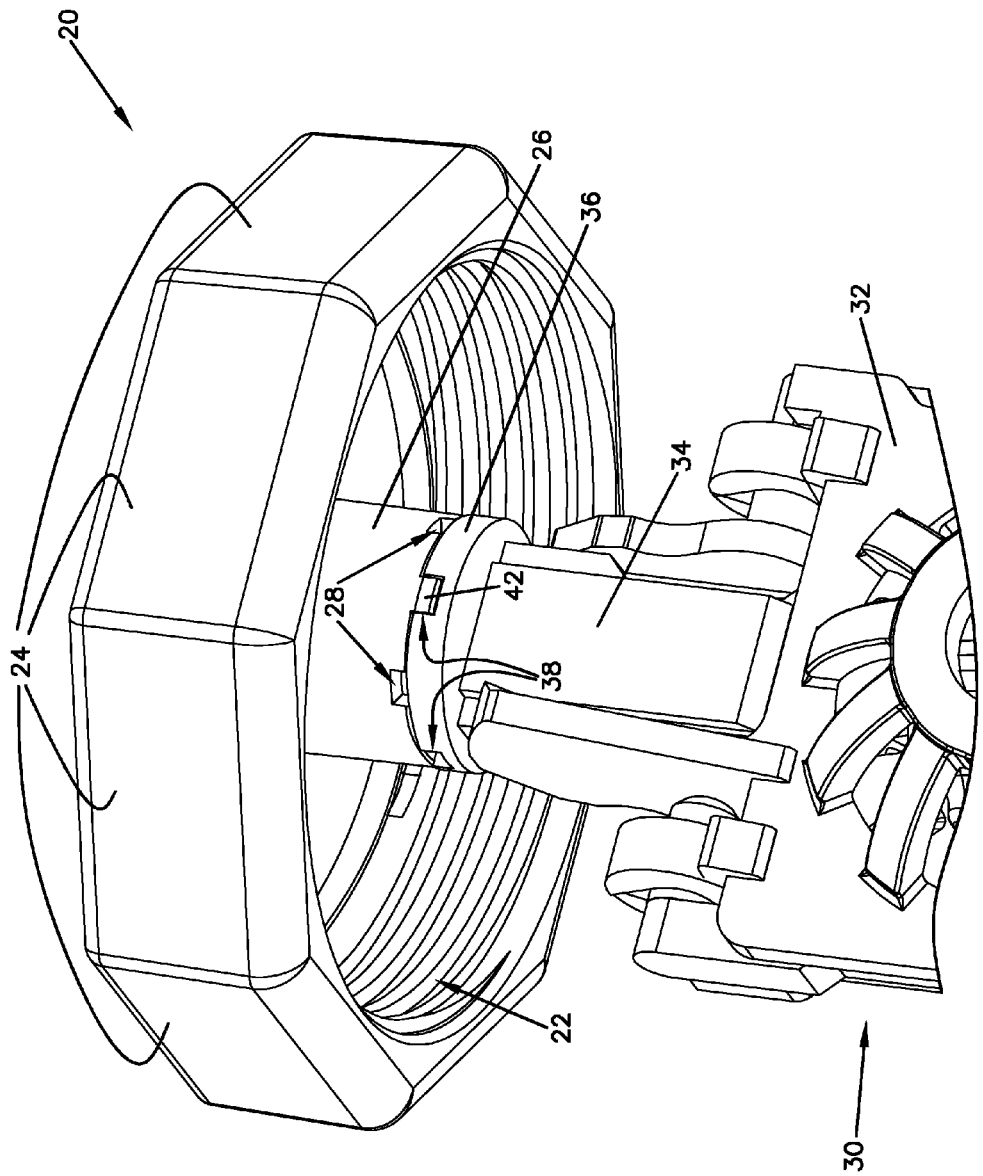
FIG. 3 is a perspective view with partial cutaway of the cap component of the lens care system of FIG. 1.

The present disclosure may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

An example lens care container 10 for cleaning with cleaning solution is illustrated in FIGS. 1-12. As illustrated, the container 10 includes a cup 100, a cap 20 and lens holder 30. The cap 20 can be a monolithic structure. The lens holder 30 can be a unitary structure. The lens holder 30 is illustrated to support a catalyst 40 disc.

The illustrated container cup 100 defines an interior chamber accessible through a top opening bounded by a rim 105. The interior chamber holds a volume of cleaning and/or disinfection solution. The catalyst disc 40 interacts with the cleaning and/or disinfection solution when the cap 20 is inserted into the container cup 100.

The container cup 100 rim 105 includes an outer diameter. As illustrated, a connection collar 101 extends from the rim 105 along the outer surface of the container cup 100. The connection collar 101 can have a securing surface, for example threading. As illustrated, the threaded connection collar surface 101 can have a channel 103 of unthreaded sections to provide a discharge channel for gas vented from the container during use, as will be described further below. The unthreaded channel 103 can extend generally linearly from the rim of the container cup 100 through the length of the threaded surface 101.

The illustrated container 10 also includes a cap 20 that is removably attachable to the container cup 100 to cover the opening. The cap 20 includes a top panel 21, a coupling hub 26, and a collar 24. The illustrated collar 24 includes an inner diameter that extends transversely from the top panel 21. The inner diameter of the collar 24 is configured to receive the outer diameter of the collar 101 of the container cup 100.

The top panel 21 includes a pressure-release vent 23 that is positioned within a deflection region 27. The deflection region 27 is defined by an annular geometry, for example a ring, of reduced thickness recessed away from the interior gas vent path 37.

The coupling hub 26 defines an interior gas vent path 37 that extends from the top panel 21 and is bounded by an open distal end with an anti-rotation mechanism 42 and at least one channel vent 28. As illustrated, the cap pressure-release vent 23 includes an aperture extending through the top panel 21. The illustrated cap pressure-release vent 23 aperture can also include a funneled mouth 29 that leads from the inner surface of the cap 21.

The illustrated lens holder 30 includes a stem 33 with an anti-rotation mechanism 38 that cooperates with the cap anti-rotation mechanism 42 to prevent rotation of the cap 20 with respect to the lens holder. The illustrated stem 33 also includes a seal 35 which can sealably engage the cap pressure-release vent 23 when the cap 20 and lens holder 30 are received within the container cup 100. The illustrated lens holder seal 35 can include a dome 39 extending from the stem 33, such that the dome sealably engages the inner circumference of the cap pressure-release vent 23 aperture. The illustrated lens holder seal 35 can also include a chamfered ring 41 surrounding the dome 39. The chamfered ring 41 sealably inserts into the funneled mouth 29 on the pressure-release valve 23.

Figure 5A:
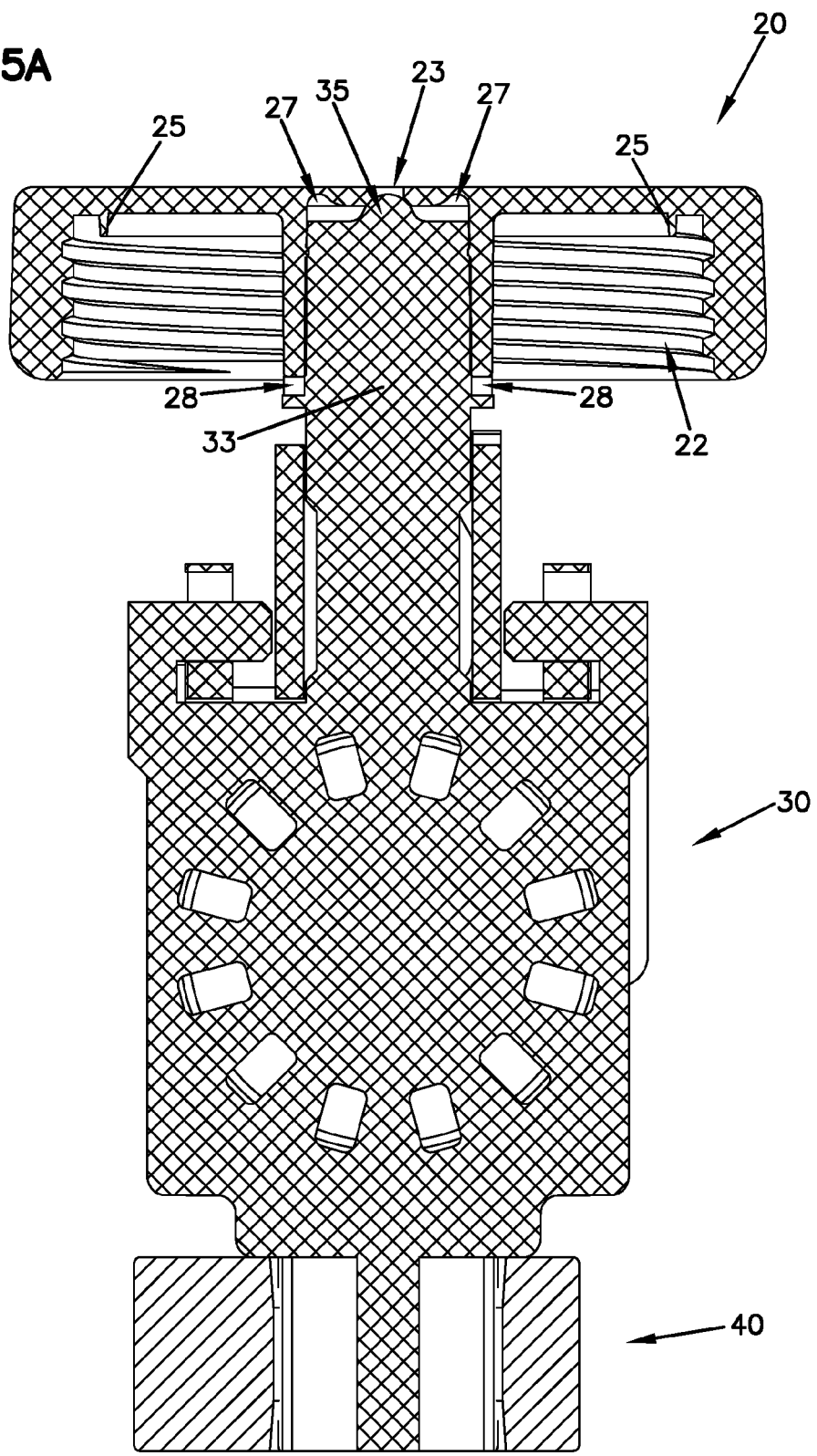
FIG. 5A is a cross sectional view of the contact lens holder component of FIG. 2 in a sealed state.
Figure 5B:
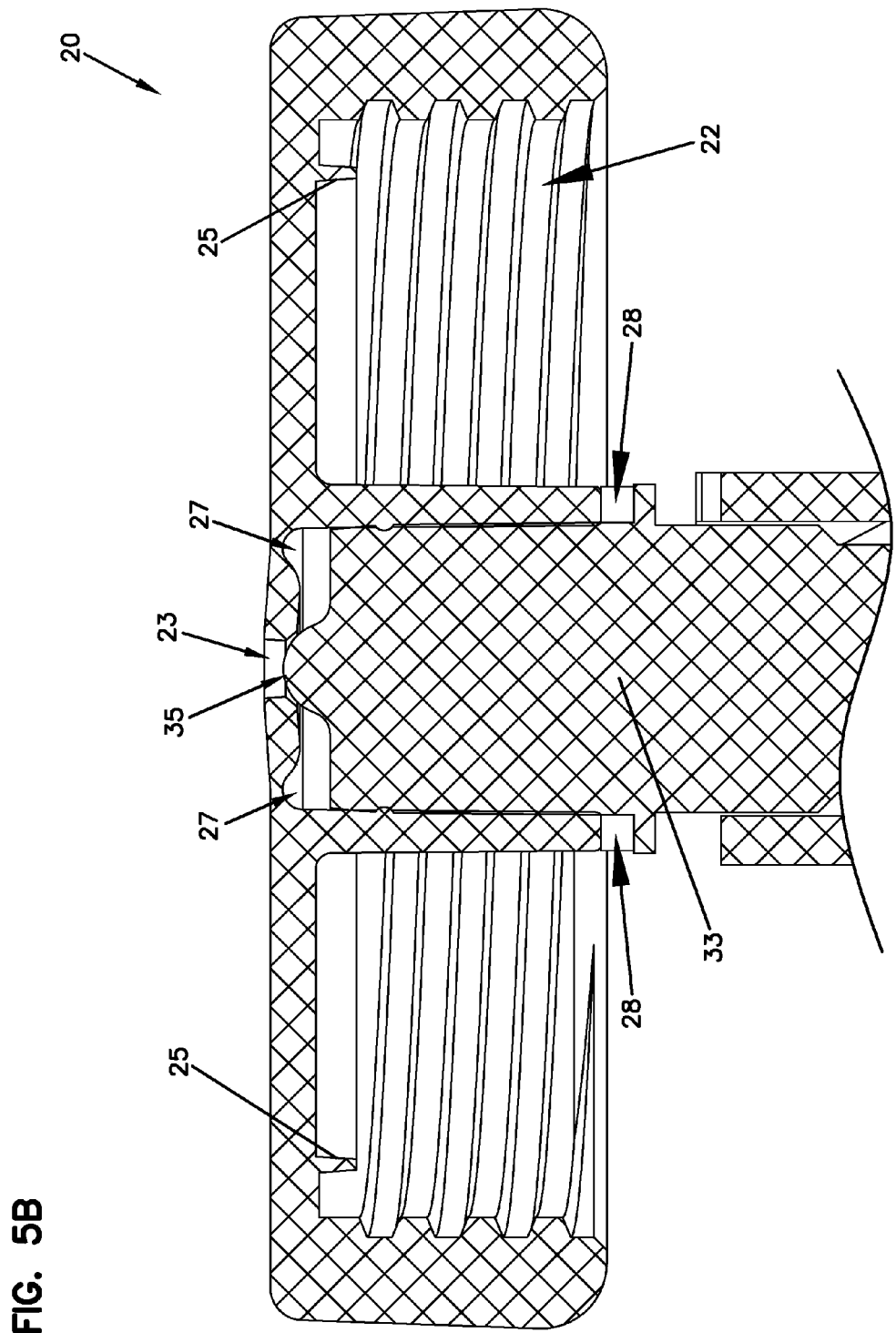
FIG. 5B is a cross sectional view of the contact lens holder component of FIG. 5A in an unsealed state.
Figure 6:
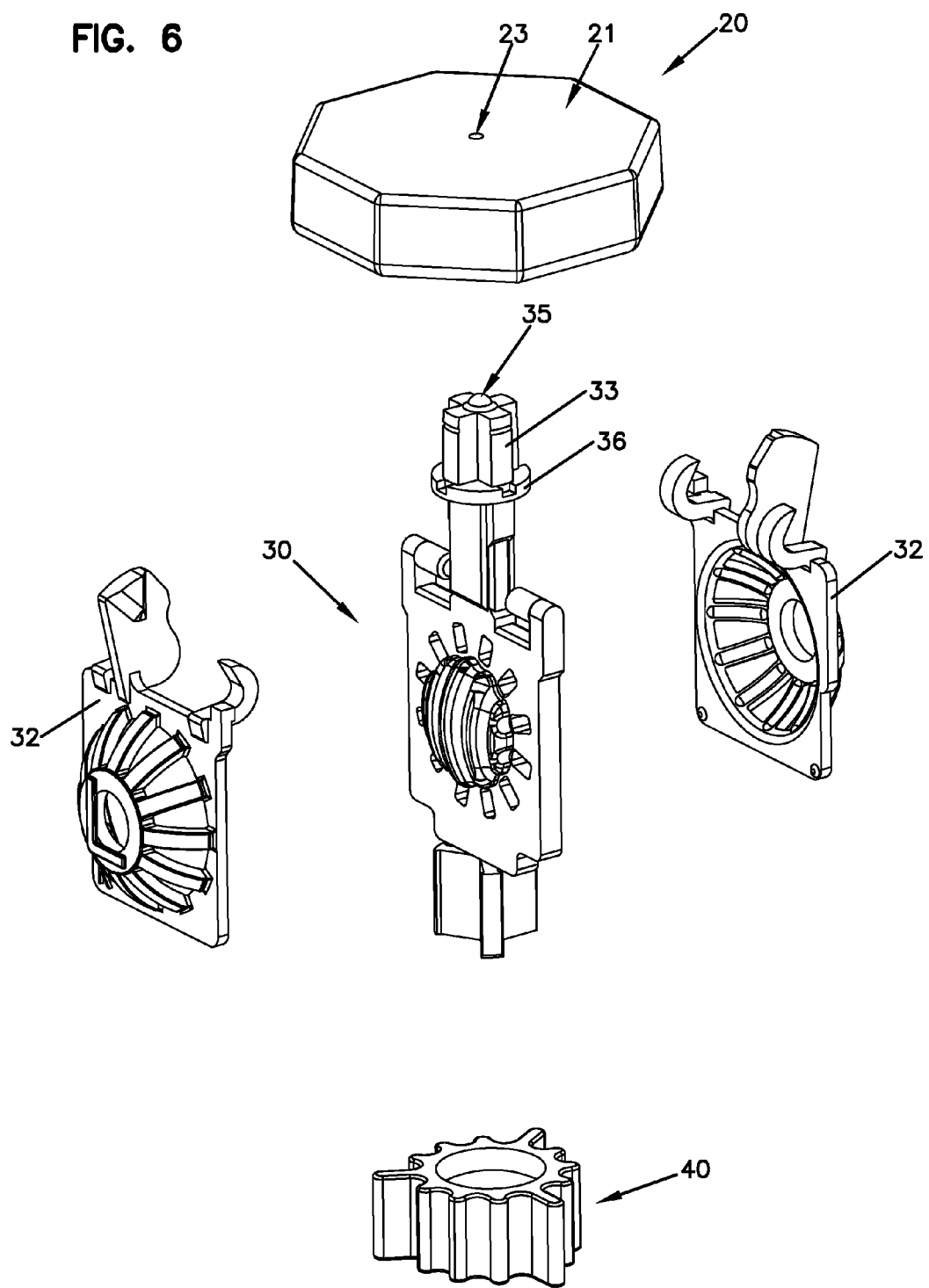
FIG. 6. is an exploded view of the contact lens holder component of FIG. 2.
Figure 7:
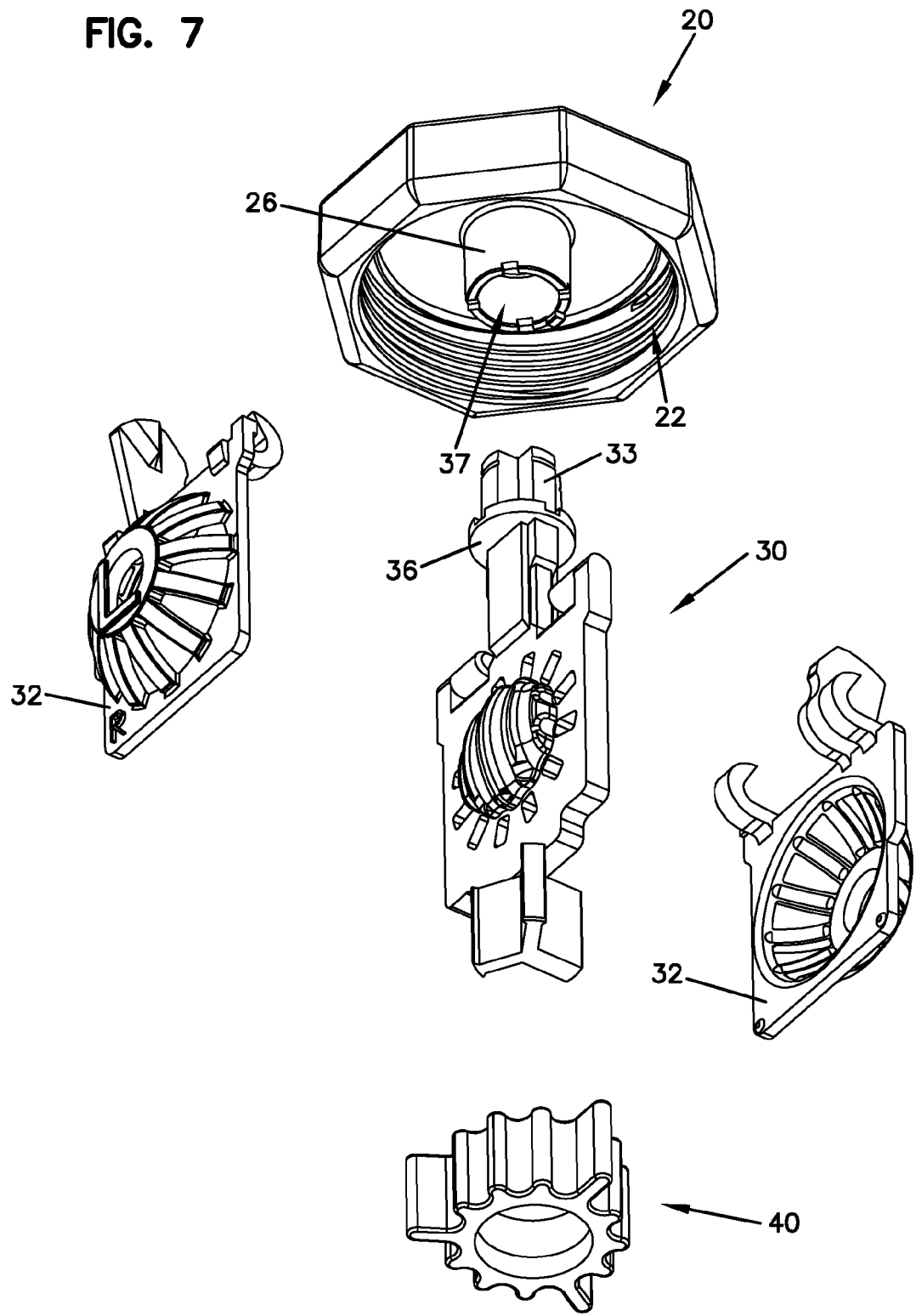
FIG. 7. is an underneath exploded view of the contact lens holder component of FIG. 2.
Figure 8:
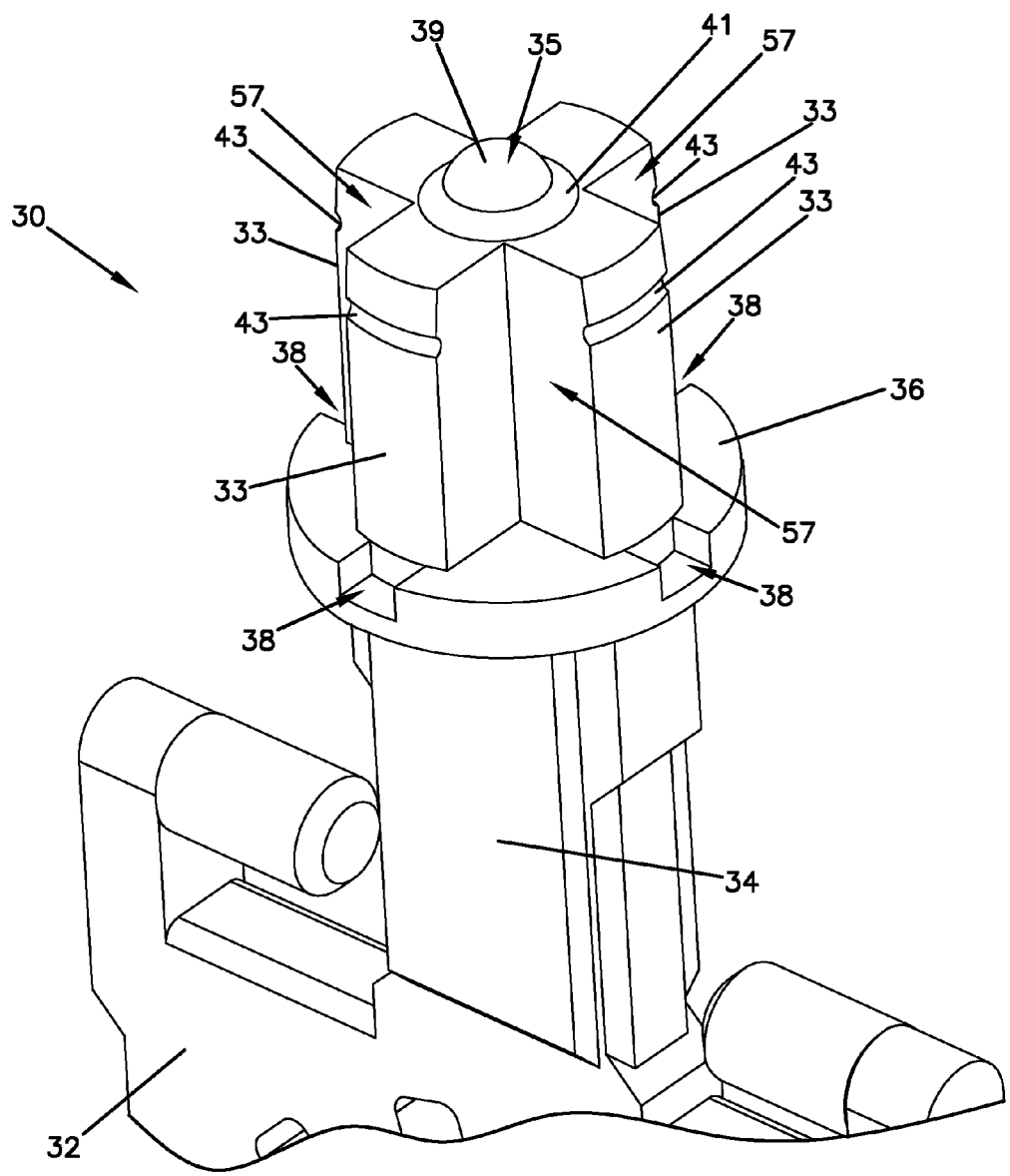
FIG. 8. is a perspective cut away view of the stem and neck of the contact lens holder component of FIG. 2.
Figure 9:
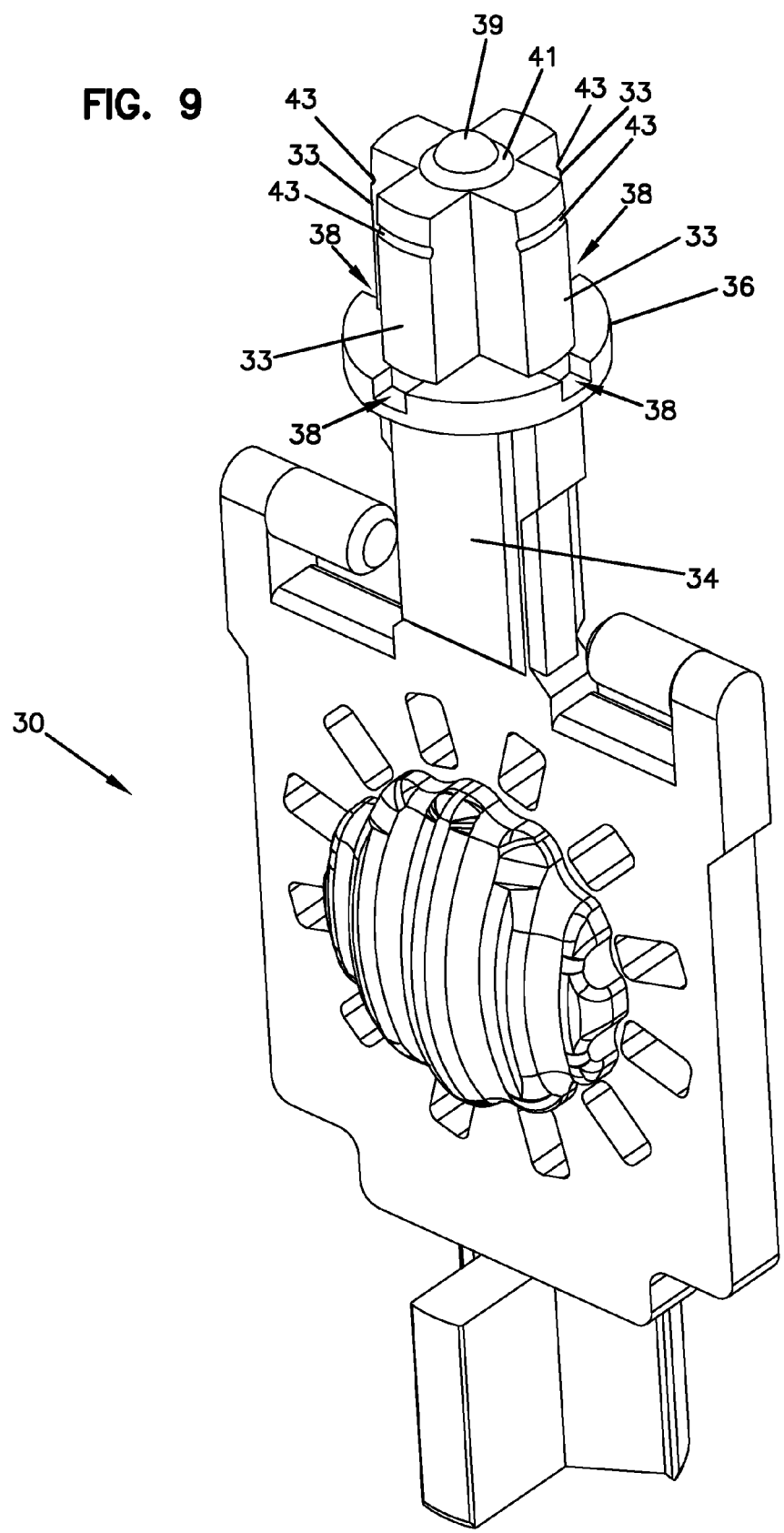
FIG. 9. is a perspective view of the stem and neck of the contact lens holder component of FIG. 2.
Figure 10:
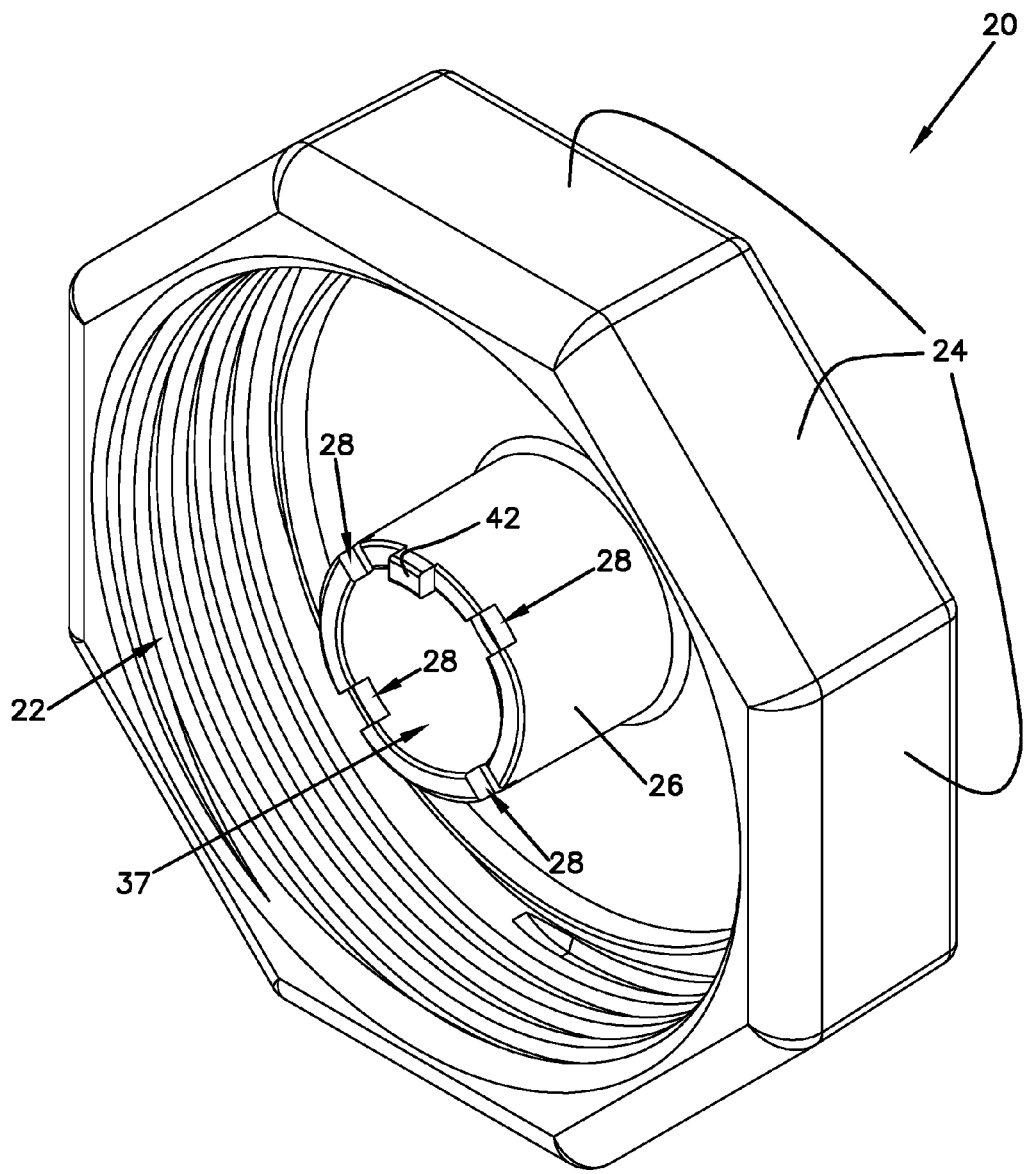
FIG. 10 is a perspective view of the cap removed from the stem and neck of the contact lens holder component of FIG. 2.
Figure 11:
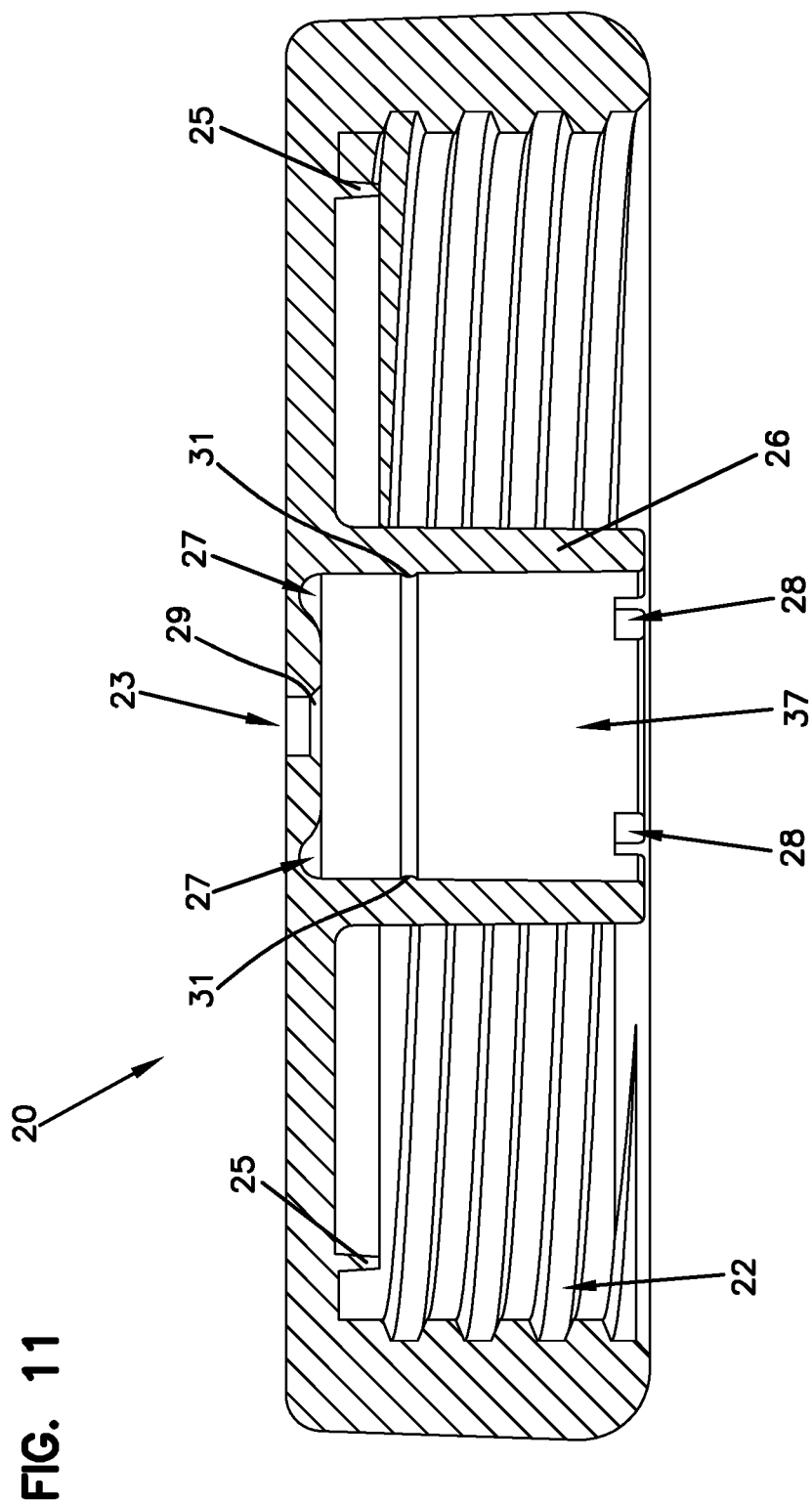
FIG. 11 is a cross-sectional view of the cap of FIG. 10.
Figure 12:
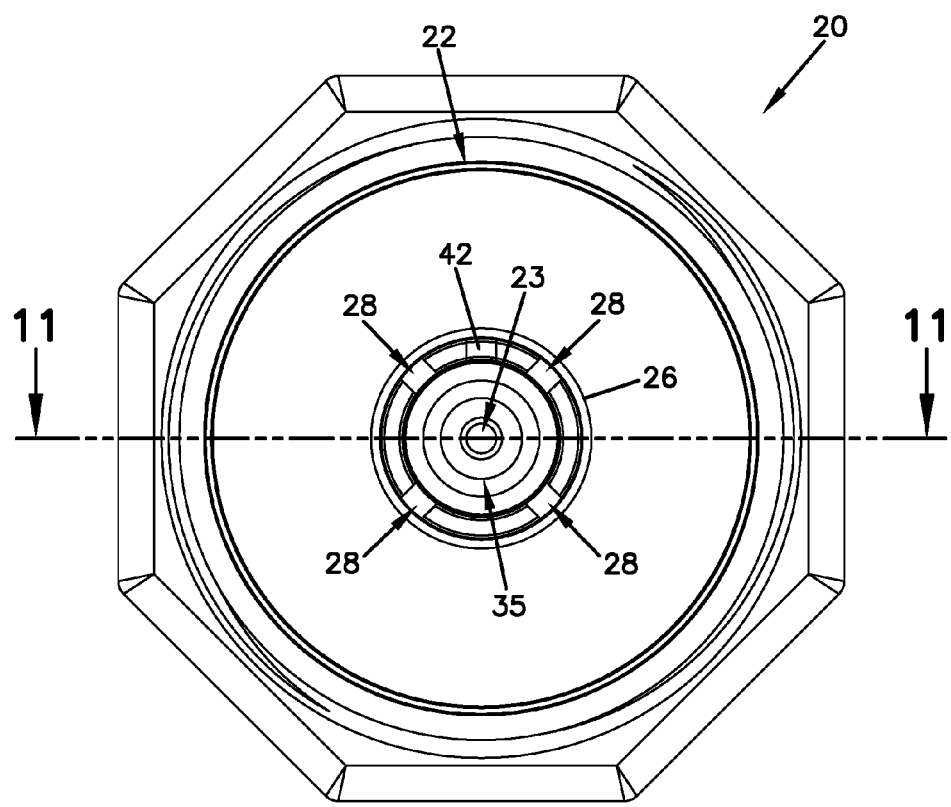
FIG. 12 is a bottom view of the cap of FIG. 10.

As particularly depicted in FIG. 5A, when the catalyst disc 40 interacts with the cleaning and/or disinfection solution in the container cup 100, a volume of gas passes through the channel vents 28 into the interior gas vent path 37. This escaping gas applies an outwardly-directed force against the deflection region 27 of the cap 21. As particularly depicted in FIG. 5B, this application of force flexes the cap top surface 21 and disengages the lens holder seal 35 from the cap pressure-release vent 23 to allow the gas to exit through the cap pressure-release vent.

The illustrated lens holder stem 33 also includes at least two passageways 37. The at least two passageways 37 can be defined by at least two intersecting plates. As illustrated, the at least two intersecting plates support the lens holder seal 35. When the lens holder 30 is secured to the cap 20, the at least two passageways in the stem 33 can be aligned with the interior gas vent path 37 in the hub 26 to allow free passage of the gas entering through the at least one channel vent 28.

As illustrated, the cap anti-rotation mechanism 42 includes a male orientation key, and the lens holder anti-rotation mechanism 38 includes a female receiver to receive the cap anti-rotation mechanism orientation key.

As illustrated, the cap coupling hub 26 can include a snap ring 31, for example a ridge, protruding within the interior gas vent path 37. The lens holder stem 33 can include a snap groove 43 to receive the snap ring 31.

As illustrated, the lens holder 30 can also include a pair of repositionable lens baskets 32. The lens holder 30 can also include a neck 34 that extends between the pair of lens baskets 32 and the stem 33. The stem 33 also includes a radial flange 36 that extends between the neck 34 and the stem 33. The lens holder anti-rotation mechanism 38 can be defined within the radial flange 36.

As illustrated, the cap top panel 21 can also include a rim wall 25 extending within the collar 24. The rim 105 of the container cup 100 is received between the cap collar 24 inner diameter and the rim wall 25.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

What is claimed is:

1. A system for releasing a contained volume of gas, the system comprising:
    a cap with a top panel comprising a pressure-release aperture positioned within a flex region, wherein the cap top panel flex region comprises a relaxed state and a flexed state;
    a seal to disengagably seal the pressure-release aperture, the seal comprising a gas vent path that extends from the pressure-release aperture;
    wherein the contained volume of gas passes through the gas vent path to apply force against the cap top panel flex region to deflectibly disengage the cap top panel flex region away from the seal, allowing the gas to exit through the pressure-release aperture.

2. The system of claim 1, wherein the seal comprises a dome, such that the dome sealably engages the inner circumference of the aperture.

3. The system of claim 2, wherein the seal comprises a chamfered ring surrounding the dome, and the aperture comprises a funneled mouth facing the gas vent path, the funneled mouth receiving the dome and the chamfered ring.

4. The system of claim 1, wherein the flex region is defined by an annular ring of reduced thickness.

5. A lens care container comprising:
    a container defining an interior chamber;
    a cap removably attachable to the container, the cap comprising a pressure-release vent positioned within a deflection region defined between a geometry of reduced thickness; and
    a lens holder comprising a seal to sealably engage the cap pressure-release vent.

6. A system for releasing a volume of gas from a container comprising a contained volume and a connector, the system comprising:
    a cap removably attachable to the container connector to enclose the volume of gas, the cap comprising a top panel, the top panel comprises a pressure-release vent positioned within a deflection region, wherein the cap top panel deflection region comprises a relaxed state and a deflected state; and
    a coupling hub comprising a seal to removably seal the pressure-release vent when the cap top panel deflection region is in the relaxed state, and an interior gas vent path extending from the top panel and bounded by at least one channel vent;
    wherein the volume of gas passes through the at least one channel vent into the interior gas vent path to apply force against the deflection region and unseal the lens holder seal from the cap pressure-release vent when the cap top panel deflection region is in the deflected state, allowing the gas to exit through the cap pressure-release vent.

* * * * *